(12) United States Patent
Hamid et al.

(10) Patent No.: US 9,833,633 B2
(45) Date of Patent: Dec. 5, 2017

(54) LASER PHOTOTHERAPY DEVICE FOR ILLUMINATION OF THE SCALP TO PROMOTE HAIR GROWTH

(71) Applicants: Tamim Hamid, Pleasanton, CA (US); Richard Brewster Main, Newark, CA (US)

(72) Inventors: Tamim Hamid, Pleasanton, CA (US); Richard Brewster Main, Newark, CA (US)

(73) Assignee: Theradome, Inc., Pleasanton, CA (US)

( * ) Notice: Subject to any disclaimer, the term of this patent is extended or adjusted under 35 U.S.C. 154(b) by 115 days.

(21) Appl. No.: 14/753,000

(22) Filed: Jun. 28, 2015

(65) Prior Publication Data

US 2015/0297914 A1    Oct. 22, 2015

Related U.S. Application Data

(63) Continuation-in-part of application No. 13/928,573, filed on Jun. 27, 2013, now abandoned, which is a
(Continued)

(51) Int. Cl.
*A61N 5/067* (2006.01)
*A61N 5/06* (2006.01)

(52) U.S. Cl.
CPC ...... *A61N 5/0617* (2013.01); *A61N 2005/067* (2013.01); *A61N 2005/0626* (2013.01);
(Continued)

(58) Field of Classification Search
CPC .. A61N 5/0613; A61N 5/0616; A61N 5/0617; A61N 2005/0626;
(Continued)

(56) References Cited

U.S. PATENT DOCUMENTS

| 4,776,324 A | * | 10/1988 | Clarren | ................ A42B 3/00 |
| | | | | 2/171.2 |
| 4,867,442 A | * | 9/1989 | Matthews | .......... A61B 5/02416 |
| | | | | 482/8 |

(Continued)

*Primary Examiner* — Ahmed Farah
(74) *Attorney, Agent, or Firm* — Richard B. Main; Main Law Cafe

(57) ABSTRACT

A photo-bio-stimulation device uses near infrared (NIR) laser illumination of the scalp to promote hair growth with a lightweight user wearable device. All the remaining components are mounted on the concave underside of an outer shell. Forty to as many as eighty VCSEL laser device chips are surface mount soldered underneath of a single large, thin-layer FR4 printed circuit. These discrete devices direct a diffused, near uniform flood of 678-nanometer monochromatic laser light deep into the hair roots and follicles across the scalps of its users. Petal shapes along a central spine are cut deep into the side edges of the thin-layer FR4 printed circuit to allow it to be conformed and fixed into a hemispherical dome and attached with dozens of plastic snaps inside the outer shell. This connects inside to a rechargeable battery and power controller. A protective clear covering matching the concave underside is attached along the brims.

5 Claims, 9 Drawing Sheets

Related U.S. Application Data continuation-in-part of application No. 12/950,009, filed on Nov. 19, 2010, now abandoned.

(60) Provisional application No. 61/264,449, filed on Nov. 25, 2009.

(52) U.S. Cl.
CPC .............. *A61N 2005/0647* (2013.01); *A61N 2005/0659* (2013.01)

(58) Field of Classification Search
CPC .... A61N 2005/0627; A61N 2005/0632; A61N 2005/0635; A61N 2005/0643; A61N 2005/0645; A61N 2005/0647; A61N 2005/0651; A61N 2005/0652
USPC .............................. 607/88–91, 100, 108, 109
See application file for complete search history.

(56) References Cited

U.S. PATENT DOCUMENTS

| | | | | |
|---|---|---|---|---|
| 7,722,656 | B1* | 5/2010 | Segal | A61N 5/0617 607/88 |
| 2004/0153131 | A1* | 8/2004 | Yorke | A61N 5/0617 607/91 |
| 2010/0106077 | A1* | 4/2010 | Rabin | A61N 5/0616 604/20 |
| 2010/0242155 | A1* | 9/2010 | Carullo, Jr. | A61N 5/0617 2/171.2 |
| 2011/0060266 | A1* | 3/2011 | Streeter | A61N 5/0613 604/20 |
| 2013/0173287 | A1* | 7/2013 | Cashman | E04H 3/08 705/2 |
| 2013/0242110 | A1* | 9/2013 | Terre | H04N 5/2251 348/164 |
| 2014/0063794 | A1* | 3/2014 | Parekh | F21S 8/04 362/185 |
| 2016/0271420 | A1* | 9/2016 | Pina | A61N 5/0617 |

* cited by examiner

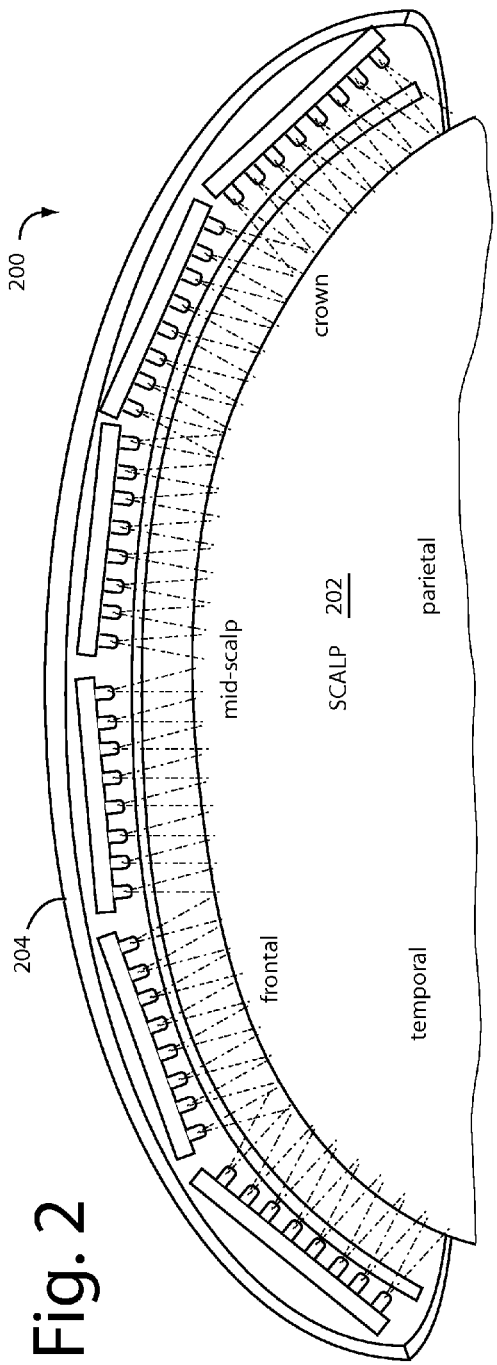
Fig. 2
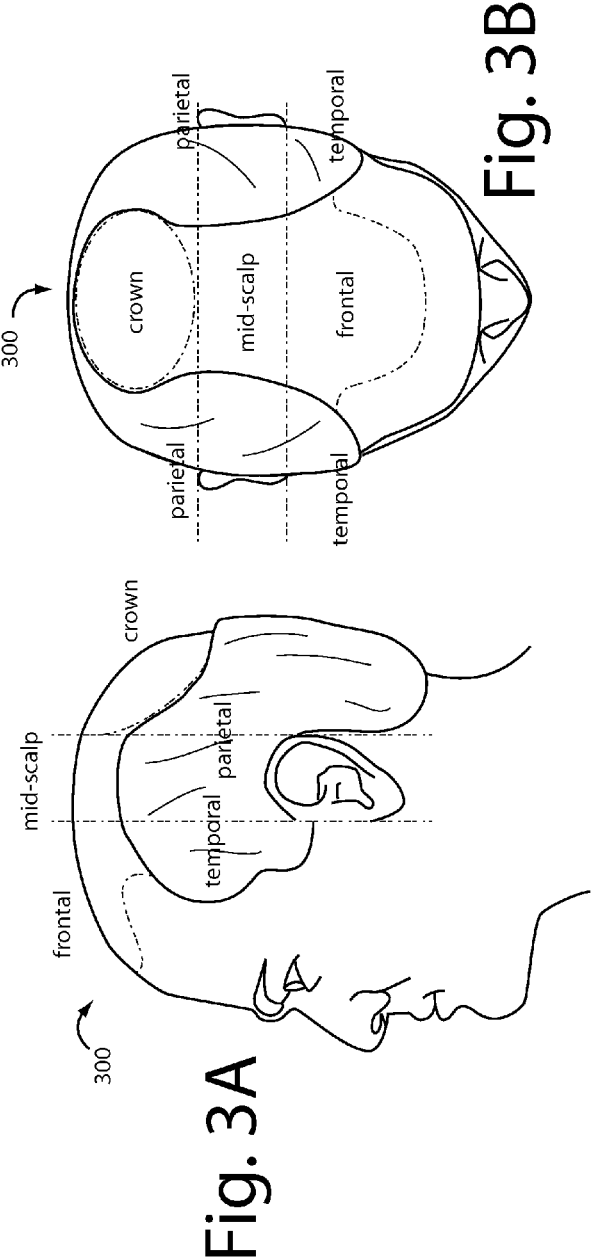
Fig. 3B
Fig. 3A

LASER PHOTOTHERAPY DEVICE FOR ILLUMINATION OF THE SCALP TO PROMOTE HAIR GROWTH

BACKGROUND OF THE INVENTION

Field of the Invention

The present invention relates to photo-bio-stimulation devices, and more particularly to near infrared laser illumination of the scalp to promote hair growth with a user wearable device.

Background

The US-FDA regulates sales of medical devices intended for the use in the diagnosis, cure, mitigation, treatment, or prevention of disease intended to affect the structure or any function of the body of humans or other animals.

Bio-stimulation lasers, also called low level laser therapy (LLLT), cold lasers, soft lasers, or laser acupuncture devices, were cleared for marketing by FDA through a Premarket Notification/510(k) process as adjunctive devices for the temporary relief of pain. These clearances were based on the presentation of clinical data to support such claims.

In January 2007, a hand-held laser therapy device was cleared by the US-FDA as a treatment for "androgenetic alopecia" (male pattern hair loss). Low Level Lasers had been previously approved by the US-FDA for the treatment for carpal tunnel syndrome, as a wound-healing aide, and as an adjunct to liposuction procedures.

Low-level laser/light therapy (LLLT), aka photo-bio-modulation and photo-bio-stimulation, has been promoted as a way to prevent hair loss and stimulate hair growth in both male and female pattern hair loss. A number of devices are marketed now for home use and are relatively simple and inexpensive. Especially when compared to conventional medical treatments and hair transplantation surgery.

SUMMARY OF THE INVENTION

Briefly, A photo-bio-stimulation device of the present invention uses near infrared (NIR) laser illumination of the scalp to promote hair growth with a lightweight user wearable device. All the remaining components are mounted on the concave underside of an outer cap shell. As many as eighty vertical cavity surface emitting laser (VCSEL) laser device chips are surface mount soldered underneath of a single large, thin-layer FR4 printed circuit. These discrete devices direct a diffused, near uniform flood of 678-nanometer monochromatic laser light deep into the hair roots and follicles across the scalps of its users. Petal shapes along a central spine are cut deep into the side edges of the thin-layer FR4 printed circuit to allow it to be cupped into a hemispherical dome and attached with dozens of plastic snaps inside the outer shell. This connects inside to a rechargeable battery and power controller. A protective clear covering matching the cupped concave side is attached along the brims.

The above and still further objects, features, and advantages of the present invention will become apparent upon consideration of the following detailed description of specific embodiments thereof, especially when taken in conjunction with the accompanying drawings.

BRIEF DESCRIPTION OF THE DRAWINGS

FIG. 2 is a schematic diagram of the VCSEL laser device arrangement over a user's scalp, according to how they were presented in FIG. 1, and represents how the dozens of discrete VCSEL laser devices can more or less uniformly flood the entire scalp with near infrared monochromatic light; and FIGS. 3A and 3B are left side and top view diagrams of a balding man illustrating the various areas of the users' scalps referred to herein;

DETAILED DESCRIPTION OF THE INVENTION

Figure 1:
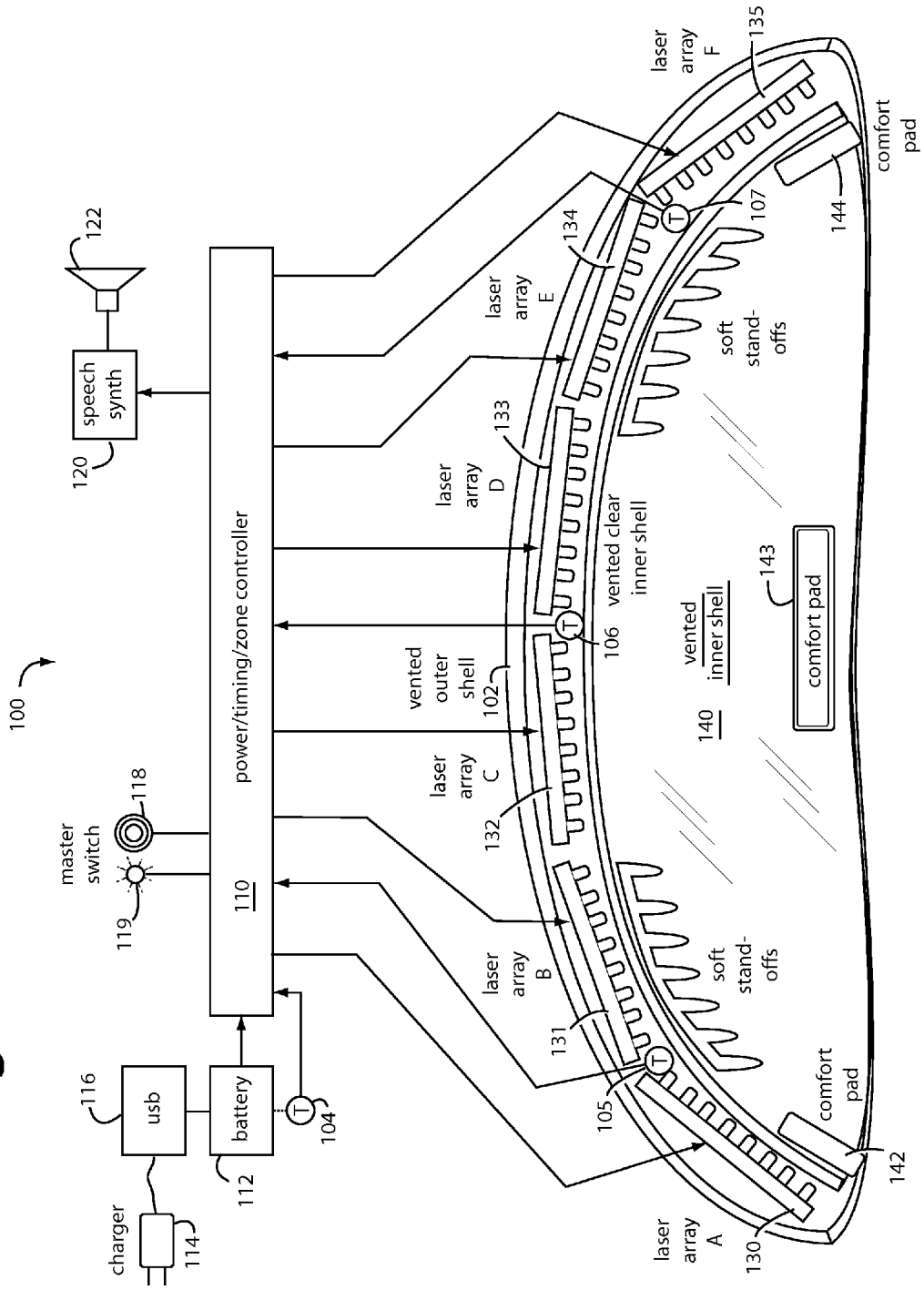
FIG. 1 is combination schematic and cutaway diagram of a light-weight, low-level laser-light scalp-hair therapy device of the present invention. The part worn by a user that faces front is shown facing left in this diagram.

FIG. 1 represents a light-weight, low-level laser-light scalp-hair therapy device 100. It is shaped and sized to be worn by a user on their head for two twenty minute sessions a week. Low-level laser-light scalp-hair therapy device 100 delivers a therapeutic doses of 678 nm monochromatic laser light deep into the hair roots and follicles. The less hair there is, the more low-level laser-light will be able to reach into the top surface layers of the scalp. Human skin tissues are translucent to light at these wavelengths.

Single wavelength monochromatic light from vertical cavity surface emitting laser (VCSEL) devices is preferred over light emitting diodes (LED's).

Human tissues are such that light at wavelengths in the near-infrared (NIR) region penetrate deeply and with minimal absorption through high scattering. A first NIR "optical tissue window" is conventionally known to admit wavelengths in the range of 650-950 nm. Longer NIR wavelengths suffer from water absorption peaks, and a dearth of NIR-CCD detectors has hindered scientific observations. A second NIR spectral window exists from 1100 to 1350 nm. A new third NIR optical window was only recently identified in the range of 1600-1870 nm. A possible fourth optical window seems to be centered at 2200 nm.

Low-level laser-light scalp-hair therapy device 100 includes an outer shell 102 that supports all the other components in one assembly. Such outer shell 102 is vented to allow heated air to escape and a cooling flow of air from beneath to circulate through. Excessive heat buildup is to be avoided, it can cause discomfort to the user, it will reduce the conversion efficiencies of the laser devices, and components like batteries can be damaged. The loss of conversion efficiencies of the laser devices not only causes battery power to be wasted, it causes less of the therapeutic laser light to be delivered into the scalp.

If excessive heat has built up, one or more of temperature sensors 104-107 will detect the event. One of these is attached to monitor battery temperature, and the others are strategically placed inside the outer shell 102. If too much heat is detected, a power/timing/zone controller 110 will turn off all the loads on a rechargeable battery 112. For example, the battery is rated for 2200-maH @ 3.7-VDC.

A popular-type USB charger 114 plugs into a micro-USB socket 116 to charge battery 112. Alternatively, a charge can be received from a conventional USB connection to a laptop computer. A master switch 118 controls basic on/off functions and can be manipulated to produce alternative operational modes in power/timing/zone controller 110. It is fitted inside with red-green-yellow LED lights 119 to visually provide operational status feedback to users. A speech synthesizer 120 and a loudspeaker 122 are included to speak instructions and status to the user. Several different languages are possible to be spoken. The vocabulary and phrases used are very simple.

An alternative technology to the use of speech synthesizer 120 are "canned" voice recordings stored in read only memory. When there are a very limited number of phrases to be spoken, as is the case here, such alternative is very inexpensive and can produce superior voice quality in any language.

Several laser arrays A-F 130-135 are mounted inside the outer shell 102 in an overhead arch. These laser arrays A-F 130-135 are generally about an inch or two square and arranged in tiles for 100% laser light coverage of the user's entire scalp. The users' scalps may be divided into zones, e.g., the frontal scalp, parietal scalp, and temporal scalp (FIGS. 3A-3B). The power/timing/zone controller 110 allows the laser arrays A-F 130-135 to be switched on/off to limit laser-light therapy to just one or more of the scalp zones. The power/timing/zone controller 110 also limits exposure times and can shut off power early if the user's scalp is not detected at all with a proximity sensor. A full therapy session is twenty minutes in duration.

In one example shown here, a total of eighty vertical-cavity surface-emitting laser (VCSEL) devices capable of delivering 3-6 joules of light energy per square centimeter of scalp are arranged on the several laser arrays A-F 130-135. Therapeutic amounts of energy delivered to the scalp appear to be in the range of 3-6 joules/cm$^2$ over a twenty minute session. About 4-6 joules/cm$^2$ of energy is considered to be optimum. The total in joules=watts per diode times the number of VCSEL's multiplied by time in seconds. The energy density, (J/cm$^2$)=watts per VCSEL multiplied by time in seconds divided by the coverage area (cm$^2$). Treatment time (secs)=energy density (J/cm$^2$)/output power density (W/cm$^2$).

Newer future products are contemplated to employ only forty VCSEL's total.

The operational distances, and thus the ambient light levels delivered by the many VCSEL's to the users' scalps must be consistent, uniform, and controlled. One centimeter spacers are used to limit the VCSEL-to-scalp separation distance. The area spacing between VCSEL's is empirically determined to provide balanced light uniformity. The power/timing/zone controller 110 is used for dynamic on/off control. It could modulate the electrical power it switches to the VCEL's to control light intensities on the users' scalps.

A vented clear inner shell 140 is mounted with spacers to the outer shell 102 and protects the several laser arrays A-F 130-135 from being rubbed, scraped, or torn by the users. A number of sponge rubber or polyurethane stick-on comfort pads 142-144 are provided loose for the users to place them inside the inner shell 140 at points they like best and that give smaller heads a comfortable fit.

Thin-layer "FR4" is used instead of traditional flexible printed circuits because the advantage of cost is so great in mass production of this consumer product. FR4 is a grade designation assigned to a type of glass-reinforced epoxy laminate sheets, tubes, rods and printed circuit boards (PCB). FR4 is a composite material composed of woven fiberglass cloth with an epoxy resin binder that is flame resistant and self-extinguishing.

FIG. 2 represents a VCSEL laser device arrangement 200 over a user's scalp 202 with a wearable device 204, according to how they were presented in FIG. 1. FIG. 2 further represents how dozens of discrete VCSEL laser devices can more or less uniformly flood the entire scalp 202 with near infrared monochromatic light Referring now to FIGS. 3A and 3B, the frontal scalp area of a typical user 300 is aft of the front hairline and back to a line drawn up in front of the ears and laterally as wide as the outside of the eyelids. The crown scalp is an oval area that starts just aft of a line drawn up in back of the ears and immediately above the upper margins of the occipital hair. The crown area is often the first and more visible area of hair thinning. The mid scalp area is the relatively flat part directly over the top and from ear to ear. Temple areas are above and forward of the ears on each side. The parietal area is between temple and occipital scalp. The occipital area lies behind the parietal area, superior to it lies the crown area and it extend below into the nape of the neck.

Figure 4:
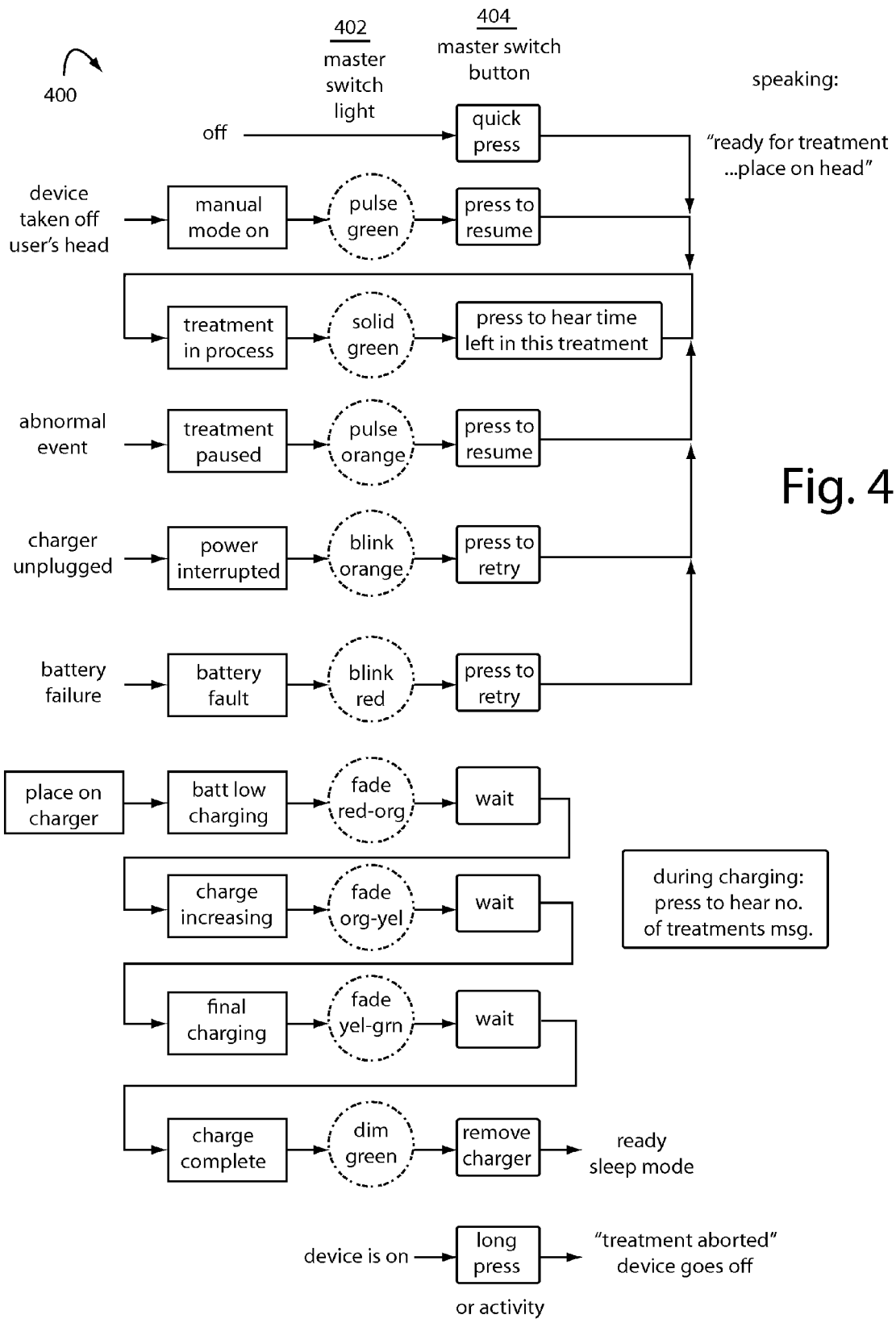
FIG. 4 is a flowchart diagram representing how the digital logic devices inside the power/timing/zone controller of FIG. 1 are ordered to function in response to the master-switch, and how the colors and durations of red-green-yellow lights mounted inside the master-switch can provide a simple but easy-to-understand operational status.

FIG. 4 uses a flowchart diagram to represent how the digital logic devices inside power/timing/zone controller 110 (FIG. 1) are ordered to function in response to the master-switch, and how the colors and durations of red-green-yellow lights 119 mounted inside the master-switch 118 can provide a simple but easy-to-understand operational status.

Figure 5:
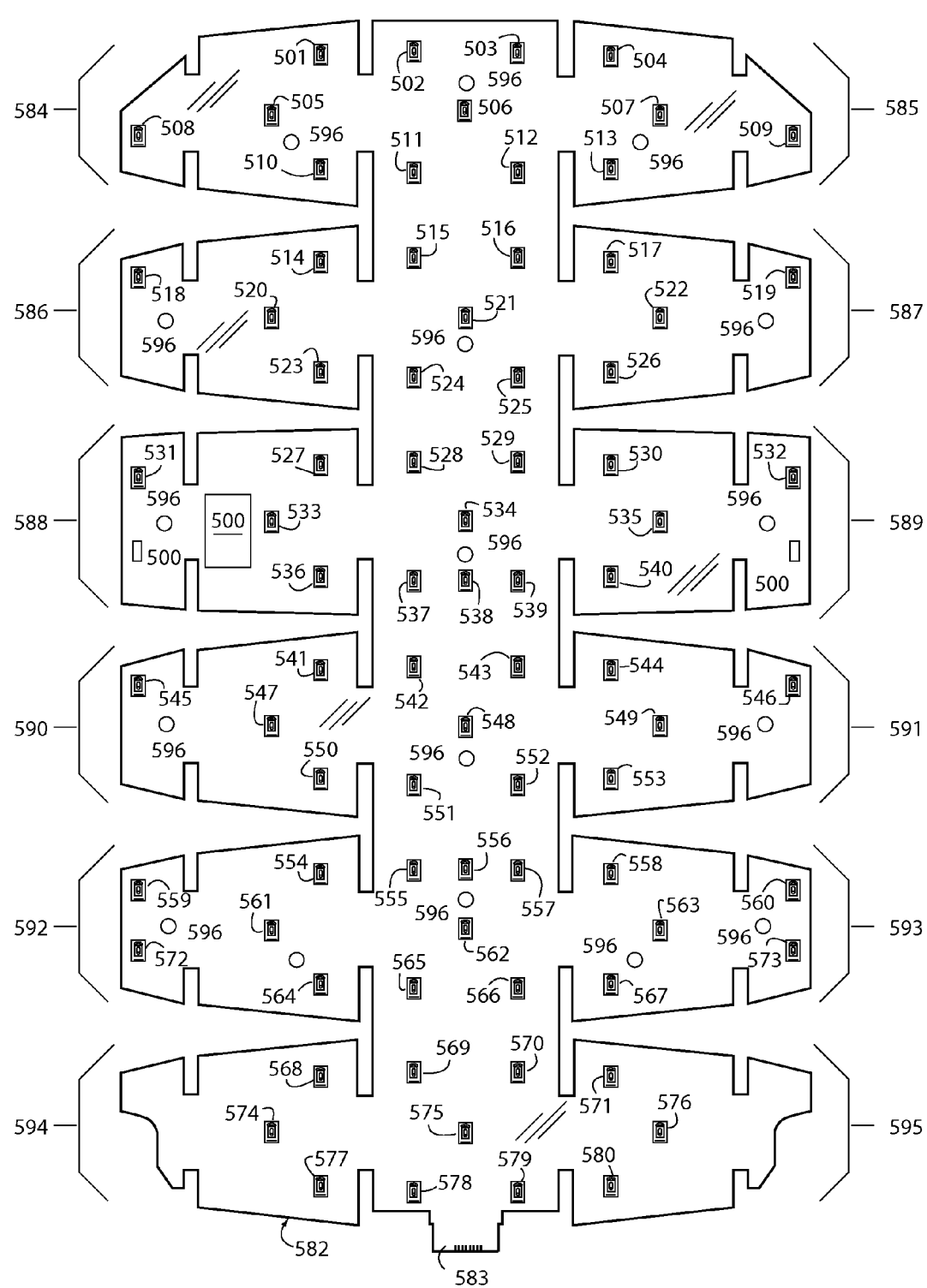
FIG. 5 is a plan view diagram of the underside of the large, thin-layer FR4 printed circuit that supports and drives the many VCSEL laser devices. The placement patterns are designed to help distribute the therapeutic light evenly and efficiency across the entire scalps of its users.

FIG. 5 represents the underside of a large, thin-layer FR4 printed circuit assembly 500 that supports and drives (here) as many as eighty surface mount soldered VCSEL laser device chips 501-580. The placement patterns are designed to help distribute the therapeutic light evenly and efficiency across the entire scalps of its users. All these VCSEL laser device chips 501-580 are attached to a single thin-layer FR4 printed circuit 582. An edge connector 583 provides the electrical connections necessary for the VCSEL laser device chips 501-580 to be powered in a number of scalp zones.

In this example, twelve "petals" 584-595 along a central spine are trimmed out deep into the side edges of thin-layer FR4 printed circuit 582 to allow it to be cupped roughly into a hemispherical dome and attached with dozens of plastic snaps inside the outer shell using holes 596. A typical thin-layer FR4 printed circuit 582 is about 7.0" wide and 13" long.

The thin-layer FR4 printed circuit assembly 500 connects inside laser-light scalp-hair therapy device 100 to the rechargeable battery 112 and power/timing/zone controller 110 (FIG. 1). A protective clear covering 140 (FIG. 1) matching the cupped concave side is attached along the edges and brims to provide a minimum scalp spacing and to prevent abrasion to the VCSEL laser device chips 501-580 during use.

A proximity circuit 597 detects when the user has removed the laser-light scalp-hair therapy device 100 from their heads, or put it back on.

Figure 6:
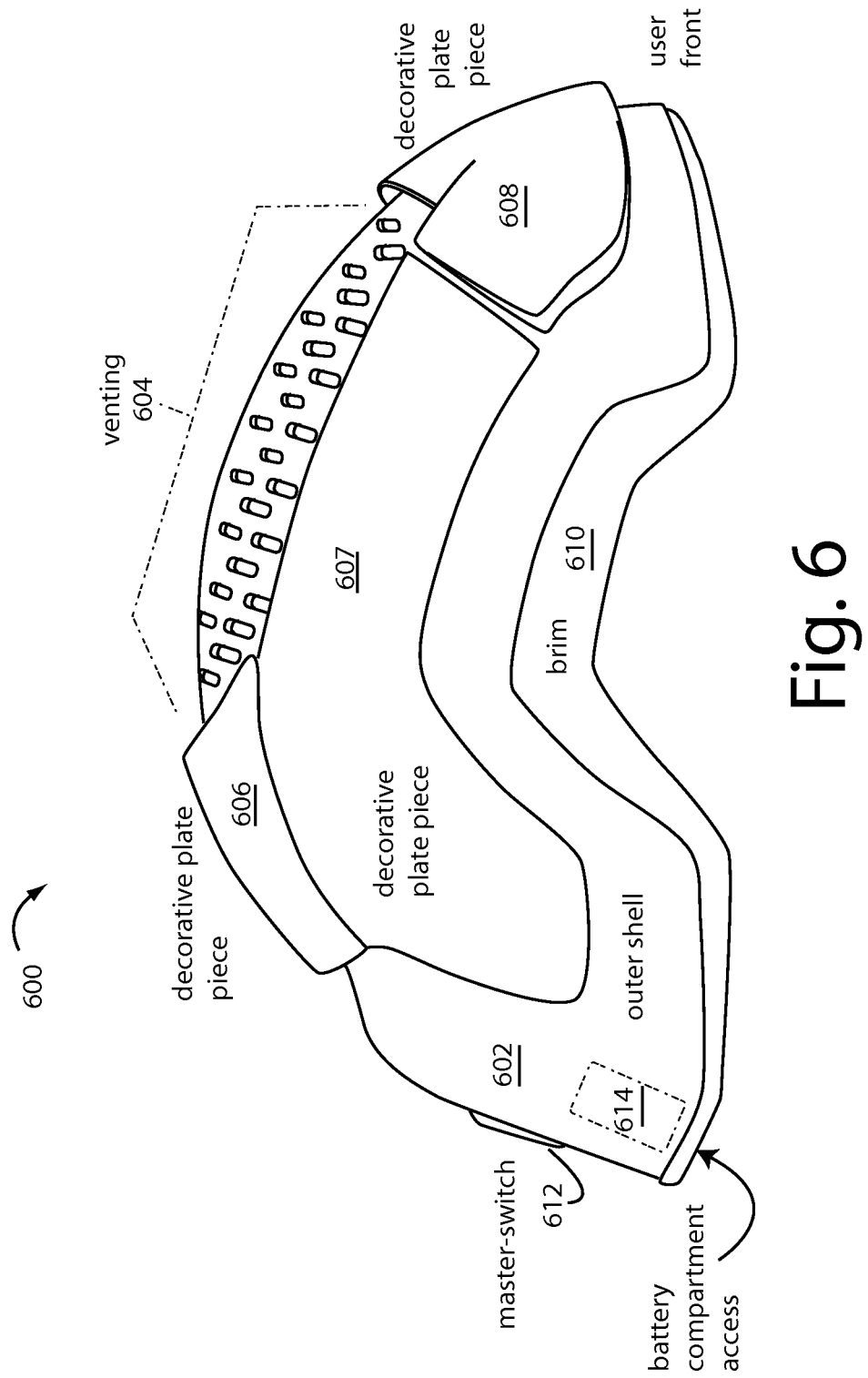
FIG. 6 is a right side view diagram of a low-level laser-light scalp-hair therapy device of the present invention for wearing on the head by a user during twenty minute treatments.

FIG. 6 represents one way that the a light-weight, low-level laser-light scalp-hair therapy device 100 can be designed for commercial appeal. Here, a light-weight, low-level laser-light scalp-hair therapy device 600 gives the general appearance of a quality bicycle helmet. It is executed in attractive white and light blue colored injection-molded plastics. Injection molding techniques lend themselves to efficient, low-cost, mass production. The whole assembly is about 11" by 8" by 6".

An outer shell 602 in white plastic has an area 604 of venting to help keep the users' heads and device 100 as cool as possible. Even a little excess heat trapped inside can cause user discomfort, fatigue, and degraded performance of the VCSEL chip devices. What appear to be simple decorative plate pieces 606-608 executed in a matching white injection molded plastic, are in fact studded underneath with bosses that protrude through reliefs in the outer shell 602 to provide dozens of standoff posts at the best angles to which thin-layer FR4 printed circuit assembly 500 (FIG. 5) can be attached during manufacturing. These same studded bosses would be very expensive and difficult to include in the production molds that make outer shell 602.

The simple decorative plate pieces 606-608 each have 2-3 Philips sheet metal fasteners that fix them solidly to outer shell 602.

A brim 610 in light blue injection molded plastic has inner shell 140 (FIG. 1) inserted into its field. The inner shell 140 is executed in clear injected molded plastic and includes dozens of vents. Brim 610 attaches to outer shell 602 with four Philips sheet metal fasteners. A master-switch 612 and a battery 614 are mounted in the rear.

Figure 7:
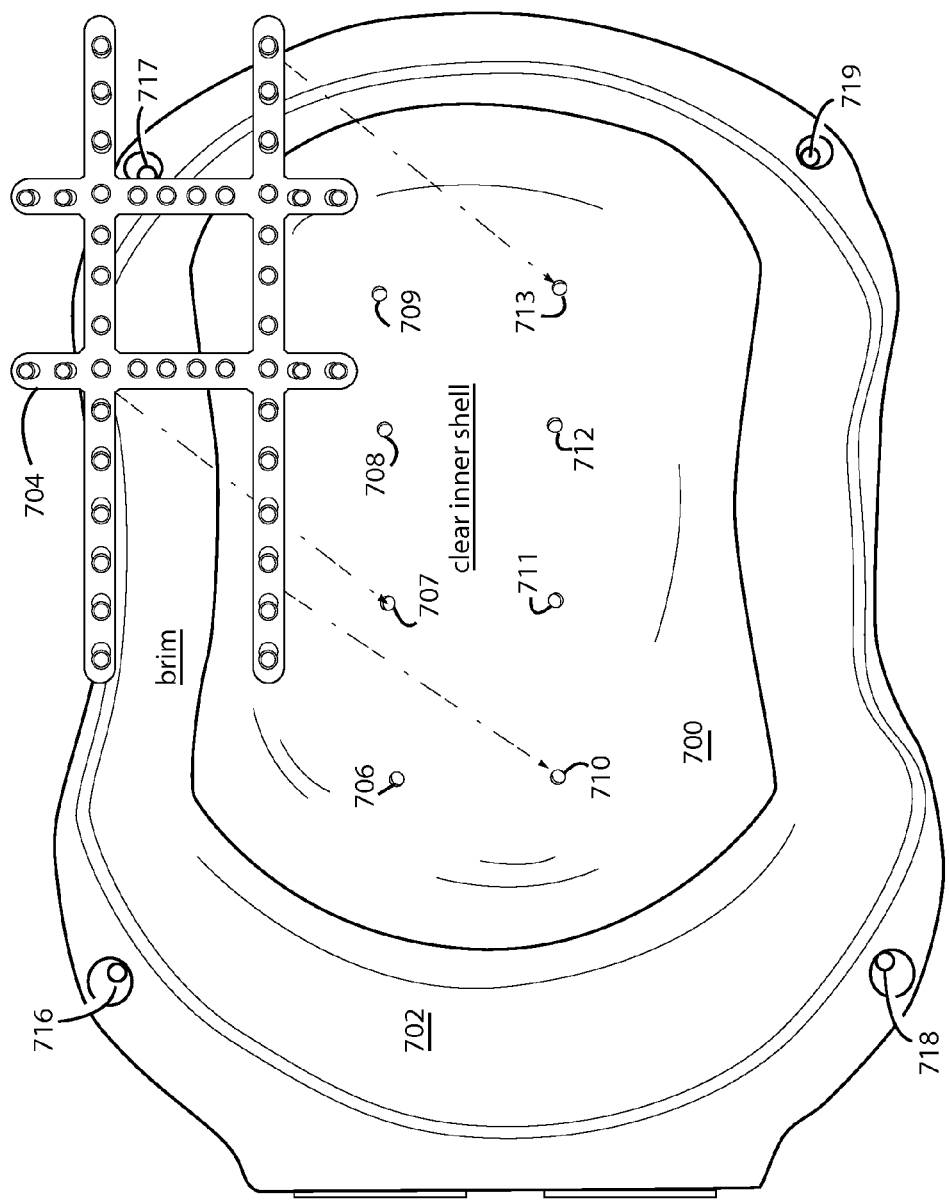
FIG. 7 is an assembly view diagram of the bottom of the clear plastic inner shell and its surrounding opaque brim. The rear of the device is to the left in the illustration. A rubber peg H-bridge is assembled inside the concave interior of the clear inner shell and retained by eight integrated rubber snap-in anchors (better seen in FIG. 8). An opaque peripheral brim joins the inner shell to the outer shell with four sheet metal screws.

FIG. 7 represents how a clear plastic inner shell 700 (140, in FIG. 1) can be molded to be joined to a surrounding brim 702 (610, in FIG. 6). A rubber peg H-bridge 704 is molded of very soft and translucent rubber, and then assembled inside the concave interior of the clear inner shell and retained by eight rubber snap-in anchors (better seen in FIG. 8) that respectively plug into eight retaining holes 706-713. The peripheral brim 702 is typically opaque, maybe light blue for aesthetic appeal, and joins the inner shell 700 to the outer shell (102, FIG. 1) with four sheet metal fastener screws using screw holes 716-719.

Figure 8:
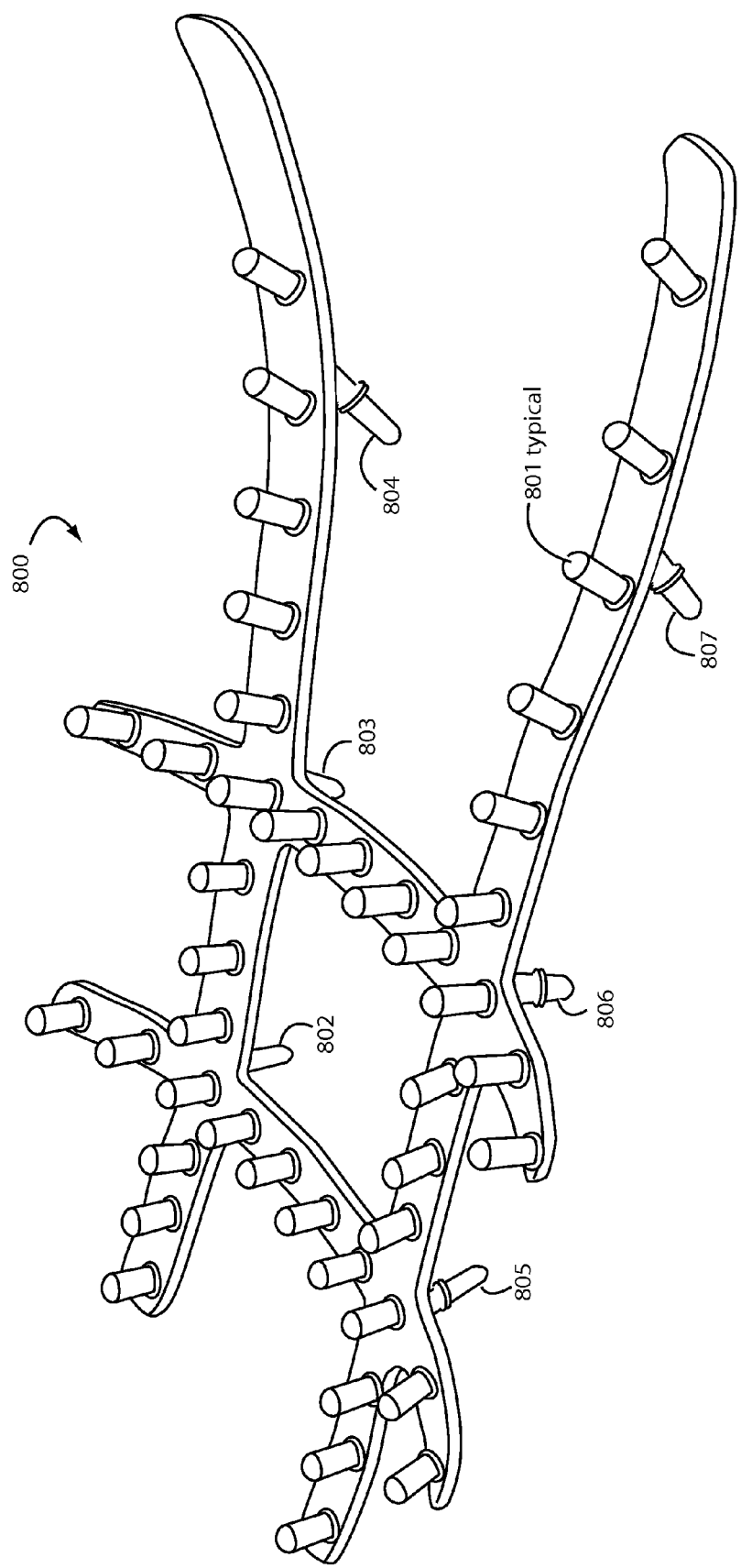
FIG. 8 is a perspective view diagram of the rubber peg H-bridge showing how the individual pegs that rest on a user's scalp are molded with various outward tilts that compensate for the bias caused to them when the whole is fitted within the concave interior of the inner shell.

FIG. 8 represents a rubber peg H-bridge 800 and the dozens of individual pegs 801 that normally point straight down and rest on a user's scalp. These pegs 801 are about 1-cm long and molded with a variety of outward tilts that compensate for the bias caused to them when the whole H-bridge 800 is fixed within the concave interior of the inner shell. The objective is shown to some extent in FIG. 1 in which the soft standoff pegs all become parallel and point straight down to align with gravity. A number of pull-through snap in anchors 802-807 are used to retain the H-bridge 800 instead of adhesives.

Figure 9:
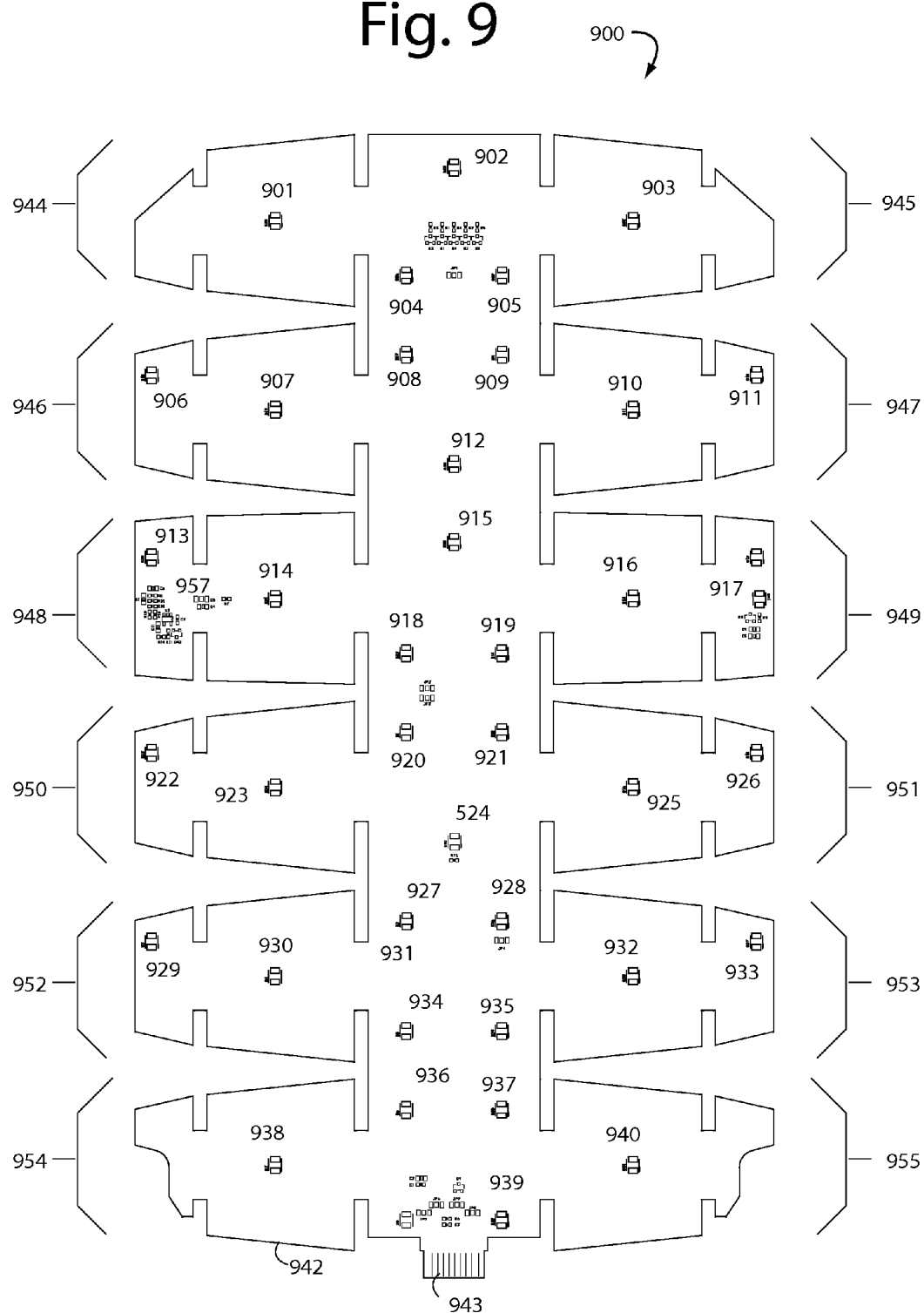
FIG. 9 is a plan view diagram of the underside of a thin-layer FR4 printed circuit with only half as many VCSEL laser devices as that of FIG. 5, in an alternative embodiment of the present invention.
Figure 10D:
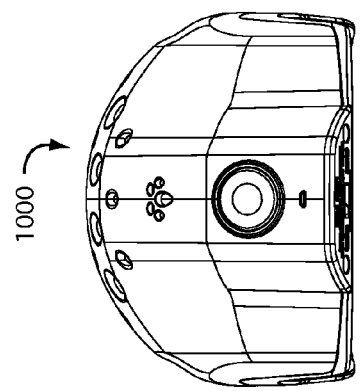
FIGS. 10A-10D are top, front, left, and rear views of an alternative outer shell for the thin-layer FR4 printed circuit with only half as many VCSEL laser devices as that of FIG. 5, in an alternative embodiment of the present invention to that shown in FIGS. 1, 2, and 6. One of the most prominent features seen here are the dozens of ventilation holes and the lack of the plate coverings necessary for simplifying the molding of the device's outer shell as shown in FIG. 6.
Figure 10A:
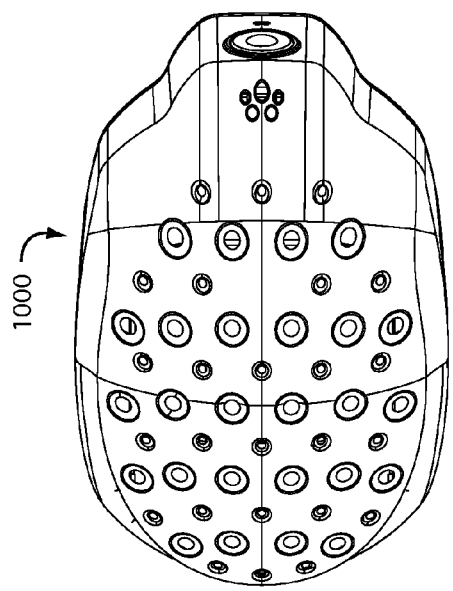
Figure 10C:
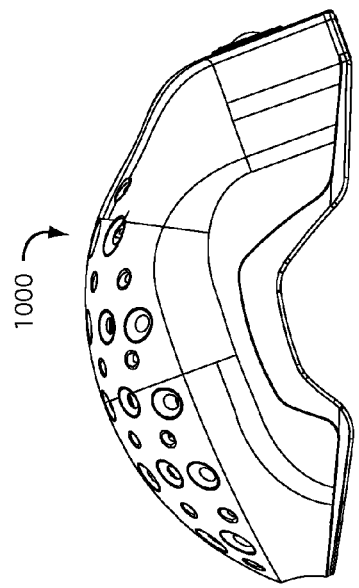
Figure 10B:
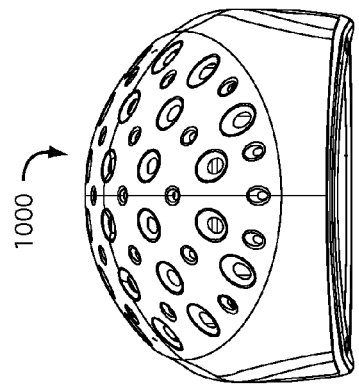

FIG. 9 represents a thin-layer FR4 printed circuit embodiment of the present invention with only half as many VCSEL laser devices as that of FIG. 5, in an alternative embodiment of the present invention referred to herein by the general reference numeral 900. Thin-layer FR4 printed circuit assembly 900 that supports and drives only half as many as surface mount soldered VCSEL laser device chips 901-940. One placement pattern designed to help distribute the therapeutic light evenly and efficiently is illustrated in FIG. 9. The VCSEL laser device chips 901-940 are typically attached to a single thin-layer FR4 printed circuit 942 using solder surface mount technology. An edge connector 943 provides the electrical connections necessary for the VCSEL laser device chips 901-940 to be powered as groups in a number of scalp zones.

Here, twelve "petals" 944-955 along a central spine are trimmed out deep into the side edges of thin-layer FR4 printed circuit 942 to allow it to be cupped roughly into a hemispherical dome and attached inside the outer shell. A typical thin-layer FR4 printed circuit 942 is about 7.0" wide and 13" long.

The thin-layer FR4 printed circuit assembly 900 connects inside laser-light scalp-hair therapy device to a rechargeable battery and power/timing/zone controller (e.g., FIG. 1). A protective clear covering matching the cupped concave side is attached along the edges and brims to provide a minimum scalp spacing and to prevent abrasion to the VCSEL laser device chips 901-940 during use.

A proximity circuit 957 detects when the user has removed the laser-light scalp-hair therapy device from their heads, or put it back on. If taken off, power to the lasers is turned off.

By way of comparison of using eighty VCSEL laser devices versus forty, TABLE I contrasts some of the more important parameters.

TABLE I

| Item | 80-VCSEL | 40-VCSEL | Comments |
|---|---|---|---|
| Laser Class | 3R | 3R | Same |
| Number of Laser Diodes | 80 | 40 | 40 in same locations in 80-VCSEL |
| Wavelength | 678 +/− 7 nm | 678 +/− 7 nm | same |
| Radiant Energy (1) | 443 J | 443 J | same |
| Radiant Power (2) | 0.36 W | 0.36 W | same |
| Treatment Time | 20 minutes | 20 minutes | same |
| Radiant Exposure | 1.03 joules/cm$^2$ | 0.52 joules/cm$^2$ | half energy delivered each session. |

TABLE I-continued

| Item | 80-VCSEL | 40-VCSEL | Comments |
|---|---|---|---|
| Total Energy Delivered | 432 joules | 231 joules | half energy delivered each session. |
| Nominal Scalp Treatment Area | 420 cm$^2$ | 420 cm$^2$ | same |
| Treatment Schedule | 2 times per week | 4 times per week | double the number of sessions per week. |
| Power Source: | Li #18650, 2200 mA, 3.7 V, length 6.5 cm | Li #18500, 1600 mA, 3.7 V, length 5 cm | slightly smaller lithium battery |
| AC Charger | 5 VDC 1.5 amp | 5 VDC 1.5 amp | same charging capability |
| Plastic Formulation Dome | | | difference only in color |
| Controller Board | TD-CONTROLLER-I | TD-CONTROLLER-I | same |
| IFU | K122950 | to be done | reflects change in model number and dome graphic, functionality and features same. |
| Firmware Revision/ Specifications | Version 109 | Version 109 | |
| FDA Section 5 510(k) Usability Requirements | K122950 | K122950 | same |
| Usability Testing | K122950 | K122950 | user interaction with device is same. |

FIGS. 10A-10D represents an alternative outer shell design for a photo-bio-stimulation device 1000. One of the most prominent features seen here are the dozens of ventilation holes that promote cooling and help avoid even a one or two degree rise in temperature inside over the ambient during use.

In general, the exact number of laser devices used is irrelevant. A few more or less will not change the therapeutic benefits. The accumulated doses they deliver to the same tissues does matter, here we suggest a radiant energy of just under 500 Joules.

Although particular embodiments of the present invention have been described and illustrated, such is not intended to limit the invention. Modifications and changes will no doubt become apparent to those skilled in the art, and it is intended that the invention only be limited by the scope of the appended claims.

The invention claimed is:

1. A low-level laser-light scalp-hair therapy device worn like a helmet on a user's head during treatments, comprising:
   a domed outer shell of plastic and with an area perforated to provide air venting to its outside;
   a thin-layer printed circuit mounted bent inside a concave bottom side of the domed outer shell;
   a plurality of vertical cavity surface emitting laser (VCSEL) device chips dispersed from one another and attached to one side of the thin-layer FR4 printed circuit;
   a controller disposed inside the domed outer shell and electrically connected to control the VCSEL's through the thinlayer printed circuit;
   a master-switch connected to the controller that provides user control of the operation of the VCSEL's;
   a battery disposed inside the domed outer shell and electrically connected to power the controller; and
   a color-variable and intensity-variable light mounted inside the master-switch and electrically connected to the controller and having digital logic that communicates the operational status of the scalp-hair therapy device by modulated color and intensity of its light.

2. The low-level laser-light scalp-hair therapy device of claim 1, further comprising:
   a speech synthesizer and loudspeaker attached to the controller that provides spoken announcements of any operational status to a user.

3. The low-level laser-light scalp-hair therapy device of claim 1, further comprising:
   a plurality of symmetrical petal cutouts in the sides of the thinlayer printed circuit along a central spine that then permit the thin-layer printed circuit to be cupped into and attached inside said concave bottom side of the domed outer shell.

4. The low-level laser-light scalp-hair therapy device of claim 1, further comprising:
   a plurality of temperature sensors connected to the controller and providing for operational power shutdowns in the event of predetermined excessive temperatures.

5. The low-level laser-light scalp-hair therapy device of claim 1, further comprising:
   separate and individual external decorative plate pieces of plastic fastened from outside the domed outer shell, and that are studded underneath with bosses that protrude through a corresponding plurality of reliefs in the domed outer shell to provide standoff posts at angles to attach inside the thin-layer printed circuit.

\* \* \* \* \*